US006255536B1

(12) United States Patent
Worm et al.

(10) Patent No.: US 6,255,536 B1
(45) Date of Patent: Jul. 3, 2001

(54) FLUORINE CONTAINING VINYL ETHERS

(75) Inventors: Allan T. Worm, N. St. Paul; George G. I. Moore, Afton; Miguel A. Guerra, Woodbury, all of MN (US); Werner Schwertfeger, Bavaria (DE); Klaus Hintzer; Zai-Ming Qiu, both of Woodbury, MN (US); Erik D. Hare, St. Paul, MN (US)

(73) Assignees: Dyneon LLC, Oakdale, MN (US); 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/470,497

(22) Filed: Dec. 22, 1999

(51) Int. Cl.$^7$ .................................................. C07F 43/11
(52) U.S. Cl. .......................... 568/615; 568/616; 568/685
(58) Field of Search .................................... 568/615, 616, 568/685

(56) References Cited

U.S. PATENT DOCUMENTS

| 2,713,593 | 7/1955 | Brice et al. ............................ 260/535 |
| 3,132,123 | * 5/1964 | Harris et al. ........................ 260/87.5 |
| 4,273,728 | 6/1981 | Krespan ............................ 260/465.6 |
| 4,379,901 | 4/1983 | Amimoto et al. .................... 526/247 |
| 4,433,180 | 2/1984 | von Werner .......................... 568/684 |
| 4,513,128 | 4/1985 | Uschold ................................ 526/212 |
| 5,326,917 | 7/1994 | Feiring et al. ........................ 526/247 |
| 5,350,497 | 9/1994 | Hung et al. ....................... 204/157.92 |
| 5,449,825 | 9/1995 | Ishibe et al. .......................... 562/851 |
| 5,466,877 | 11/1995 | Moore .................................. 562/852 |
| 5,476,974 | 12/1995 | Moore et al. ........................ 568/677 |
| 5,488,142 | 1/1996 | Fall et al. .............................. 560/227 |
| 5,589,557 | * 12/1996 | Navarrini et al. .................... 526/247 |

FOREIGN PATENT DOCUMENTS

| 0 290 848 | 11/1988 | (EP) .............................. C07C/43/17 |
| WO 98/50603 | 11/1998 | (WO) .............................. C25B/3/08 |

OTHER PUBLICATIONS

"Modern Fluoropolymers", John Scheirs, Wiley Series in Polymer Science, 1997, pp 376–378.
Emel yanov et al, Zh. Org. Khim, (1994) 30(8), pp. 1266–1270.
D. Sianesi et al., J. Org. Chem., vol. 31 (1966), p. 2312.

* cited by examiner

Primary Examiner—Paul F. Shaver
(74) Attorney, Agent, or Firm—James V. Lilly

(57) ABSTRACT

The present invention describes a novel process for the preparation of perfluorovinyl ethers. The process involves providing a hydrocarbon precursor that may be partially halogenated, fluorinating the precursor to provide a perfluorinated intermediate, and converting the perfluorinated intermediate to the desired perfluorinated ether. Novel perfluorovinyl ethers are also provided.

10 Claims, No Drawings

FLUORINE CONTAINING VINYL ETHERS

FIELD

The present invention relates to perfluorinated vinyl ethers and to the preparation thereof. These monomers are valuable comonomers for fluoroelastomers with enhanced low temperature properties.

BACKGROUND

The benefits of modifying fluoropolymers by vinyl ethers are described in various review articles. See, for example, Modern Fluoropolymers, John Scheirs, Wiley Series in Polymer Science 1997 and in other literature (e.g. Emel 'yanov et al, Zh. Org. Khim (1994) 30(8) 1266–70; Krespan, Carl G., DuPont de Nemours U.S. Pat. No. 4,273,728).

Partly fluorinated vinyl ethers and their copolymers are described in A. E. Feiring et al, DuPont de Nemours U.S. Pat. No. 5,326,917. Long chain vinyl ethers provide in fluoroelastomers excellent low temperature properties (see Uschold et al, U.S. Pat. No. 4,513,128).

The preparation of perfluoro(alkyl vinyl ethers) by fluorination with elemental fluorine is known. See Hung et al, U.S. Pat. No. 5,350,497. This patent discloses the fluorination of selected partially fluorinated (di)chloroethyl ethers (followed by dehalogenation to the corresponding perfluoro (alkyl vinyl ether).

Perfluorinated long chain perfluoroethers are difficult to prepare, especially those vinyl ethers without branching and more than 3 atoms in the alkyl group. For example, perfluorovinyl ethers are commonly prepared by two routes. See, for example, Modern Fluoropolymers, J. Scheirs, Wiley 1997 pp 376–378.

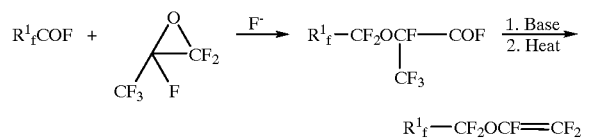

Addition of perfluorinated acid fluorides to hexafluoropropylene oxide results in an acid fluoride that may be converted to a salt and pyrolyzed to give the described perfluorovinyl ether. The oligomerization of hexafluoropropylene oxide with itself and conversion to a salt and subsequent pyrolysis gives long chain but branched ethers.

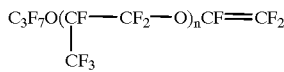

A more recent process prepares perfluorovinyl ethers by using perfluoro alkyl hypofluorites and dichlorodifluoroethylene followed by dehalogenation using, for example, Zn.

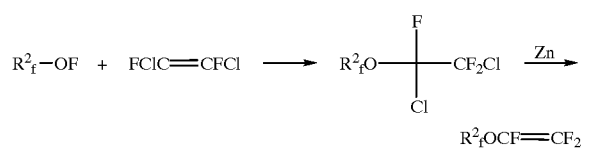

As noted, it is difficult to provide long chain perfluorinated ethers, especially vinyl ethers, when using these processes. A difficulty in the dichloro process includes the hazards of making and handling the $R^2{}_f$—OF species. Because of these hazards, this species also has a limited availability. An improved process for making perfluorinated vinyl ethers is needed, particularly for making linear perfluorinated vinyl ethers.

SUMMARY

The present invention describes a process for the preparation of a perfluorinated vinyl ether of the formula $CF_2=CF-O-R_f$ wherein $R_f$ is a linear, branched or cyclic perfluorinated aliphatic group that may contain oxygen atoms thereby forming additional ether linkages. $R_f$ groups containing such oxygen atoms are referred to as perfluoroalkyleneoxy groups. $R_f$ preferably contains from 1–20, more preferably from 1 to 10, carbon atoms in the backbone. $R_f$ may also contain sites of terminal unsaturation.

Preferably, the perfluorinated ethers prepared according to the invention are selected from perfluorinated linear vinyl ethers of the formula $CF_2=CF-O-R_f$. In one embodiment, the vinyl ethers are preferably free of chlorine atoms.

The process of the invention comprises the steps of:
  (a) providing a hydrocarbon precursor comprising at least one 2-alkoxypropionate moiety, derivative, or equivalent that may be partially halogenated,
  (b) fluorinating the hydrocarbon precursor to provide a perfluorinated intermediate,
  (c) converting the perfluorinated intermediate to its corresponding perfluorinated acid metal salt, and
  (d) converting the perfluorinated acid metal salt to its corresponding perfluorovinyl ether.

As used herein, the term perfluorinated means that all of the carbon bonded hydrogen atoms have been replaced with fluorine and any unsaturated carbon—carbon bonds have been saturated with fluorine.

In a first embodiment of the process of the invention, an appropriate hydrocarbon (e.g., containing at least one 2-alkoxy propionate moiety, derivative or equivalent) precursor is provided which includes a hydrocarbon acid derivative. Such derivatives include, for example, acid fluorides, anhydrides, esters and the like. This derivative is then perfluorinated to provide a corresponding perfluorinated acid derivative intermediate. The intermediate is then converted to its corresponding perfluorinated acid metal salt and subsequently converted to the desired perfluorovinyl ether.

In a second embodiment of the invention, a partially fluorinated hydrocarbon precursor is provided by reacting hexafluoropropylene oxide with an alcohol or a species such as sodium alkoxide. The precursor is then fully fluorinated by replacing any remaining carbon bonded hydrogen atoms with fluorine atoms to provide a perfluorinated acid derivative intermediate. The intermediate is then converted to its corresponding perfluorinated metal salt and subsequently converted to the desired perfluorovinyl ether.

In a third embodiment of the invention, a partially fluorinated hydrocarbon precursor is provided by reacting a fluorinated olefin with an alcohol, 2) fully fluorinating the precursor, 3) hydrolyzing the fluorinated precursor to an acid derivative, 4) converting the acid derivative to its corresponding perfluorinated acid metal salt, 5) converting the salt product to its corresponding perfluorovinyl ether.

In a fourth embodiment of the invention a perfluorovinyl ether having the formula $R_fOCF_2OCF=CF_2$ is provided wherein $R_f$ is as described above.

DETAILED DESCRIPTION

The perfluorinated vinyl ethers prepared according to the present invention are useful in the preparation of fluoroelastomers, especially those that are used at low temperatures. Such elastomers are known. See, for example, Uschold et al., U.S. Pat. No. 4,513,128.

The embodiment selected is not critical to the practice of the invention. However, there are certain process steps common to each of the embodiments of the invention.

Fluorination of the precursors may be accomplished by either electrochemical fluorination (ECF) or direct fluorination (DF). ECF is described in U.S. Pat. No. 2,713,593 and WO 98/50603. DF is described in U.S. Pat. No. 5,488,142.

Conversion of the perfluorinated precursor to the metal salt is preferably accomplished by treatment with a base, e.g. saponification.

Conversion of the perfluorinated metal salt to the vinyl ether is preferably accomplished by pyrolysis. Typically this is done by drying the salt and then heating the salt to a temperature of from 170° C. to 250° C. with or without the presence of a solvent or other medium.

The following discussion specifically addresses three embodiments of the invention. It is not intended to limit the scope of the disclosure to these embodiments. Rather it illustrates the versatility of the process.

In the first embodiment of the invention, the perfluorovinyl ether may be prepared by
(a) providing a hydrocarbon ester, anhydride, acid halide or acid precursor which comprises at least one 2-alkoxypropionate moiety, derivative or equivalent,
(b) fluorinating the precursor to provide a perfluorinated acid derivative intermediate,
(c) converting the perfluorinated intermediate to its perfluorinated metal salt, and
(d) pyrolyzing the perfluorinated metal salt to the corresponding perfluorovinyl ether.

More specifically, the first embodiment may be exemplified by the following synthesis sequence:

where $R_h$ is a $C_1$–$C_{20}$ alkyl or aromatic group, which may be linear, branched, cyclic and which may contain additional ether linkages. The $X_h$ moiety is selected from the group consisting of $R_h$, lower alkoxy, (such as —$OCH_3$, —$OCH_2CH_3$), $OC(O)CH(CH_3)OR_h$, —F and —Cl. $R_f$ is a perfluorinated version of $R_h$ and $X_f$ is a perfluorinated version of $X_h$.

In the case where a divinyl ether is desired, a precursor may be represented as

where $R'_h$ is described in a similar manner to $R_h$ above except it is divalent. The $R_h$ moieties in this particular precursor may be the same or different. Such a divinyl ether is $CF_2=CFOR'_fOCF=CF_2$ wherein $R'_f$ is a perfluorinated version of $R'_h$.

In an additional possibility, the pendant methyl group of the —$CH(CH_3)COO$— moiety may contain a chlorine atom. This chlorine atom will survive the fluorination step and may provide some reactive advantage in subsequent steps.

When $R_f$ is linear, this route opens new possibilities for the synthesis of long chain, non-branched vinyl ether in an efficient and economical way and is not limited to certain sequences in the side chain. In contrast see, for example, Masahiro et al, Daikin EP 290,848 where the molecule is limited to a repetition of the sequence (—$OCF_2CF_2CF_2$—).

An alternate approach to the hydrocarbon precursor for this embodiment involves esters of 2-alkoxy-1-propanol. This precursor has the configuration of the ester moiety reversed when compared to the first reaction sequence listed, but is functionally equivalent to a 2-alkoxypropionate in the process of this invention. The precursor is then perfluorinated as described above. The resulting species then is dissociated to produce the perfluoro-2-alkoxy propionyl fluoride. From this point the conversion to the vinyl ether proceeds as in the first reaction sequence by converting the propionyl fluoride to the corresponding perfluorinated metal salt and pyrolyzing the salt to the corresponding perfluorovinyl ether.

An additional precursor which may be used in this route includes

where $R^3$ is an alkyl group which may contain additional ether linkages and

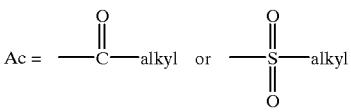

with the alkyl being a $C_1$–$C_6$ alkyl group. Preferably, the alkyl is a $C_1$ alkyl group that may be fluorinated. The chlorine on the pendent methyl group will also survive the fluorination process.

The hydrocarbon containing precursors are either commercially available or are easily prepared by common organic synthesis. Corresponding long chain polyether alcohols may be coupled with 2-chloropropionic acid to achieve the desired precursors, but any other method is also useful. Examples of ester precursors for fluorination include $CH_3OCH(CH_3)COOCH_3$
$[CH_3OCH(CH_3)CO]_2O$
$CH_3OCH(CH_3)CH_2OCOCH_3$
$CH_3OCH(CH_3)CH_2OCOCF_3$
$CH_3OCH(CH_3)CH_2OSO_2CF_3$
$CH_3OCF(CF_3)COOCH_3$
$[CH_3OCF(CF_3)CO]_2O$
$CHF_2OCH(CH_3)COOCH_3$
$CH_3OCH(CH_2Cl)COOCH_3$
$HCF_2CF_2OCH(CH_3)COOCH_3$
$CF_3CH_2OCH(CH_3)COOCH_3$
$CH_3OCH_2OCH(CH_3)COOCH_3$
$C_2H_5OCH_2OCH(CH_2Cl)CH_2OCOCH_3$
$CH_3OCH_2CH_2OCH(CH_3)COOCH_3$
$CH_3OCH_2CH_2CH_2OCH(CH_3)COOCH_3$
$CH_3OCH(CH_3)CH_2CH_2OCH(CH_3)COOCH_3$
$C_2H_5OCH_2CH_2CH_2CH_2OCH(CH_3)COOCH_3$
$CF_3OCF_2CHFCF_2OCH(CH_3)COOCH_3$
$CF_3OCHFCF_2OCH(CH_3)COOCH_3$
$CF_3CHFCF_2OCH(CH_3)COOCH_3$
$C_2H_5OC_2H_4OC_2H_4OCH(CH_3)COOCH_3$
$nC_3F_7CH_2OCF(CF_3)COCl$
$nC_3F_7CH_2OCF(CF_3)COF$
$(CH_3)_2CHCH_2OCH(CH_3)COOCH_3$
$C_8H_{17}OCH(CH_3)COOCH_3$
$C_8F_{17}C_2H_4OCH(CH_3)COOCH_3$
$C_6H_5OCH(CH_3)COOCH_3$ 4-CH$_3$OC$_6$H$_4$OCH(CH$_3$)COOCH$_3$
CF$_3$OCFHCF$_2$OCH$_2$OCH(CH$_3$)CO$_2$CH$_3$ Fluorination of the precursors can be done by electrochemical fluorination (ECF) as previously described. ECF may be operationally simpler because only one reactor is used. However, ECF tends to give lower yields of some species because of C—O and C—C bond cleavage reactions.

In contrast, direct fluorination (DF) conducted according to U.S. Pat. Nos. 5,476,974 or 5,488,142 leads to little or no rearrangement and only minor losses attributable to cleavage reactions. Thus, in spite of the need for both a fluorine generator and a direct fluorination reactor, DF is preferred in most cases because of a higher yield of the desired product. Some partially fluorinated precursors, such as 2,3,3,3-tetrafluoropropionic derivatives of the second embodiment give little rearrangement and less cleavage in ECF than the unfluorinated precursors.

The resulting perfluorinated esters, anhydrides or acid fluoride end groups may be converted to the corresponding hydrocarbon methyl esters with methanol if a separation step (e.g. distillation) is desired to purify the reaction product. This is typically done to separate the perfluorinated compounds from the reaction media. Either the separated product or the perfluorinated products in the reaction mixture are then saponified with bases, i.e. converted to a salt, (e.g. KOH, Na$_2$CO$_3$, NaOH) to give the resulting salts. The salts are then dried and pyrolyzed at temperatures from 170° C. to 250° C. with or without solvent to give the corresponding perfluorovinyl ether. The resulting perfluorovinyl ether is preferably purified by distillation to obtain the desired purity.

In a second embodiment of the invention a partially fluorinated hydrocarbon precursor is used. This precursor is prepared by reacting hexafluoropropylene oxide with an alcohol (such as is described in D. Sianesi et al., J. Org. Chem., Vol. 3 (1966), p. 2312).
This process comprises the steps of:
(a) providing a partially fluorinated hydrocarbon precursor by reacting hexafluoropropylene oxide with an alcohol,
(b) perfluorinating the precursor, for example, by electrochemical or direct fluorination, to provide a perfluorinated ester or acid intermediate,
(c) converting the perfluorinated intermediate to its corresponding metal salt, and
(d) pyrolyzing the perfluorinated salt at a temperature sufficient to provide a perfluorovinyl ether.
This process is represented by the following synthesis sequences.

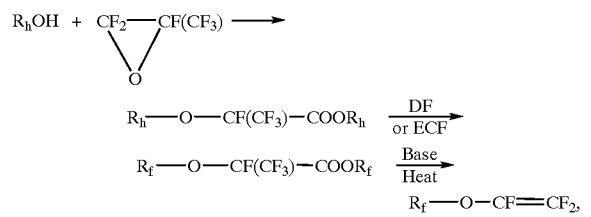

wherein R$_f$ and R$_h$ are as described above.

The fluorination, conversion to a salt and pyrolysis to the perfluorovinyl ether are done in a manner similar to that described in the first embodiment.

In a third embodiment of the invention, a perfluorinated vinyl ether may be prepared by a process comprising the steps of:
(a) providing a partially fluorinated precursor which is a reaction product of a fluorinated olefin and an ester of lactic acid,
(b) perfluorinating the precursor, to provide a corresponding perfluorinated ester or acid derivative intermediate,
(c) converting the perfluorinated intermediate to its corresponding metal salt, and
(d) pyrolyzing the perfluorinated salt to the corresponding perfluorovinyl ether.

More specifically, the third embodiment of the invention is exemplified by the following synthesis sequences.

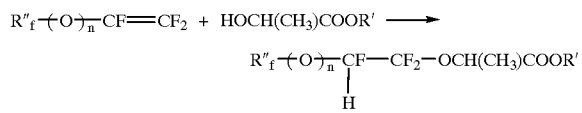

where n=0 or 1, and R''$_f$ is F or R$_f$ when n is 0, and R''$_f$ is R$_f$ when n is 1, and R' is an C1 to C6 alkyl.

Preferred olefins for the addition to the hydrocarbon ester are tetrafluoroethylene, hexafluoropropene, perfluoro(alkyl vinyl) ethers, such as perfluoro(methyl vinyl) ether, perfluoro(propyl vinyl) ether or other perfluoro vinyl ethers as described herein. The preferred bases to catalyze the addition are alkali hydroxides KOH, NaOH, or NaOMe. Solvents for the reaction include N,N-dialkyl carboxylic acid amides, such as those disclosed in U.S. Pat. No. 4,433,180 (von Werner). The 2-alkoxy propionate moiety is supplied by the hydrocarbon ester in this embodiment.

The resulting partially fluorinated precursors are fluorinated to provide a perfluorinated acid derivative intermediate. This step may be accomplished by either ECF or DF as discussed above. The solvents for the direct fluorination embodiments are perfluorinated compounds and/or fluorochloro compounds, e.g. perfluoromethylmorpholine, Freon-113, etc.

The perfluorinated intermediate is then converted to a metal salt. The salt is then pyrolyzed to the corresponding perfluorovinyl ether. These steps are accomplished in a manner similar to that described in the first embodiment.

Examples of perfluorinated vinyl ethers made according to one or more of the methods described above include
CF$_3$O(CF$_2$)$_3$OCF=CF$_2$
and R$_f$—OCF$_2$OCF=CF$_2$, including CF$_3$OCF$_2$OCF=CF$_2$
and C$_2$F$_5$OCF$_2$OCF=CF$_2$.

EXAMPLES

Example 1

Perfluoro(methoxyethyl)vinyl ether

Methyl 2-(methoxyethoxy) propionate was prepared by the alkylation of methoxyethanol (1500 g, 19.7 m) with 2-chloropropionic acid (1050 g, 9.7 m), using NaOH (790 g, 19.7 m) and tetrabutylammonium bromide (40 g, 0.12 m) in 1.2 liters of THF. After removal of the excess starting alcohol, methanol (965 g, 30 m) and HCl (382 g, 10.5 m) were added. Distillation gave the desired ester (832 g, 5.1 m, 53% yield) b.p. 100–120° C./15 mm identified by H-nmr. The ester was fluorinated in perfluoro-N-methylmorpholine (PMM) as described in U.S. Pat. No. 5,488,142. After fluorination, methanol (850 g, 26.6 m) was added and distillation gave methyl perfluoro 2-(methoxyethoxy) propionate (1334 g, 3.7 m, 56% yield) b. p. 111–115° C., identified by $^{19}$F NMR. The fluorinated ester (500 g, 1.39 m) was reacted with KOH (93 g, 1.4 m) dissolved in 400 g of methanol to give the corresponding salt. The salt was stripped of methanol and water at 90° C./15 mm after the addition of 21 g $K_2CO_3$ and 1000 g of Fluorinert™ FC71 (from 3M Co.). Vacuum was broken and the salt decarboxylated at 180–220° C. Perfluoro(methoxyethyl)vinyl ether was distilled (299 g, 1.06 m, 76% yield) b. p. 46–48° C., identified by $^{19}$F NMR.

Table 1 lists perfluorovinyl ethers prepared in a manner similar to Example 1 using the listed starting material. The boiling points (bp) listed were measured at atmospheric pressure.

TABLE 1

| Ex. | Starting Material | Product | Bp |
|---|---|---|---|
| 1 | $CH_3$—O—$(CH_2)_2$—O—CH(CH$_3$)—$COOCH_3$ | $CF_3$—O—$(CF_2)_2$—O—$CF=CF_2$ | 48° C. |
| 2 | $C_3H_7$—O—CH(CH$_3$)—$COOCH_3$ | $C_3H_7$—O—$CF=CF_2$ | 39° C. |
| 3 | $CH_3$—O—$(CF_2)_3$—O—CH(CH$_3$)—C(=O)—$OCH_3$ | $CF_3O$—$(CF_2)_3$—O—$CF=CF_2$ | 64° C. |

Example 4

Perfluoro(methyl vinyl) ether

Hexafluoropropylene oxide was reacted with methanol at room temperature to give in almost quantitative yield $CH_3$—O—$CF(CF_3)$—$COOCH_3$. This product was then fluorinated in perfluoro(methyl morpholine) in a tubular reactor as described in U.S. Pat. No. 5,488,142. The resulting perfluorinated compound was isolated and saponified with potassium hydroxide. The resulting salt was dried and pyrolyzed at 250° C. to give perfluoromethylvinyl ether in a 60% molar yield.

Table 2 lists vinyl ethers produced in a manner similar to Example 4, but using the listed starting alcohol. Boiling points were measured at atmospheric pressure.

TABLE 2

| Ex. | Starting Alcohol | Product | Bp |
|---|---|---|---|
| 4 | $CH_3OH$ | $CF_3$—O—$CF=CF_2$ | −23° C. |
| 5 | $C_3H_7OH$ | $C_3F_7$—O—$CF=CF_2$ | 36° C. |
| 6 | $CH_3OCH_2CH_2OH$ | $CF_3$—O—$CF_2$—$CF_2$—O—$CF=CF_2$ | 48° C. |

Example 7

Perfluoro octyl vinyl ether

In a procedure similar to Example 1, 1-octanol was converted to methyl 2-octyloxypropionate, bp 100–110 C./10 mm, and 764.5 g (3.54 mol) of this was fluorinated in a 20 liter reactor according to the procedure of U.S. Pat. No. 5,476,974 in $CF_2ClCFCl_2$ solvent. Methanolysis and distillation gave 1143 g (54%) $C_8F_{17}OCF(CF_3)COOMe$, and saponification and pyrolysis gave $C_8F_{17}OCF=CF_2$, bp 136–137° C.

Example 8

Perfluoro 3-methoxypropyl vinyl ether, $CF_3O(CF_2)_3OCF=CF_2$

In a procedure similar to Example 1, $CH_3O(CH_2)_3OH$ was converted to $CF_3O(CF_2)_3OCF(CF_3)COOMe$ bp 123–126° C. and this to $CF_3O(CF_2)_3OCF=CF_2$ bp 62–64° C.

Example 9

Perfluoro 3-methoxybutyl vinyl ether, $CF_3OCF(CF_3)C_2F_4OCF=CF_2$

In a procedure similar to Example 1, $CH_3OCH(CH_3)C_2H_4OH$ was converted to $CF_3OCF(CF_3)C_2F_4OCF(CF_3)COOMe$ bp 145–148° C. and this to $CF_3OCF(CF_3)C_2F_4OCF=CF_2$, bp 84–86° C.

Example 10

Perfluoro 2,6-dimethylcyclohexyl vinyl ether

In a procedure similar to Example 1, 2,6-dimethylphenol was converted to 2,6-$(CF_3)_2$-cyclic-$C_6F_9OCF(CF_3)$COOMe, bp 75–80° C./3 mm, and this was then converted to 2,6-$(CF_3)_2$-cyclic-$C_6F_9OCF=CF_2$ bp 136–138° C.

Example 11

Perfluoro ethoxyethoxyethyl vinyl ether $CF_3CF_2OC_2F_4OC_2F_4OCF=CF_2$

In a procedure similar to Example 1, ethoxyethoxyethanol was converted to $CF_3CF_2OC_2F_4OC_2F_4OCF(CF_3)COOMe$, bp 170–175° C., and this to $CF_3CF_2OC_2F_4OC_2F_4OCF=CF_2$, bp 92–95° C.

Example 12

Perfluoro propyl vinyl ether, $C_3F_7OCF=CF_2$

In a procedure similar to Example 1, n-propanol was converted to 2-propoxypropionic acid. This upon treatment with acetyl chloride afforded the anhydride ($C_3H_7OCH(CH_3)CO)_2O$, bp 118–22° C./15 mm, which upon direct fluorination according to U.S. Pat. No. 5,488,142 gave ($C_3F_7OCF(CF_3)CO)_2O$, bp 186–190° C. The perfluoroanhydride was methanolysed to $C_3F_7OCF(CF_3)COOMe$, bp 118–122° C. and converted to $C_3F_7OCF=CF_2$, bp 36° C.

Example 13

Perfluoro methyl vinyl ether, $CF_3OCF=CF_2$

In a procedure similar to Example 12, 2-methoxypropionic acid was converted to the anhydride ($CF_3OCF(CF_3)CO)_2O$. This was methanolysed to $CF_3OCF(CF_3)COOMe$ bp 58–62° C. and this converted to $CF_3OCF=CF_2$ bp −23° C.

Example 14

Perfluoro methyl vinyl ether from 2-methoxy-1-propyl acetate

NaH (60% in mineral oil, 8.0 g, 0.2 mol) was washed with hexane, slurried in THF, and treated dropwise with 26.4 g (0.2 mol) 1-t-butoxy-2-propanol (Aldrich Chemical) with ice cooling. The mixture was stirred at reflux one hr, chilled in ice, and treated with 19 ml (0.2 mol) dimethyl sulfate. After heating at reflux for 3 hr, the mixture was filtered, concentrated, and distilled to a head temperature of 85° C. The residue (23.9 g yellow liquid) was >90% pure 1-t-butoxy-2-methoxypropane by $^1H$ NMR analysis. Of this, 10.0 g was mixed with 0.05 g fused zinc chloride and 15 ml dichloromethane, chilled in ice, and treated slowly with 6.0 g acetyl chloride. On warming to room temperature, gas evolution was noted. The mixture was distilled to 8.0 g at about 50° C./14 Torr. $^1H$ NMR and gc/ms confirmed 2-methoxy-1-propyl acetate in >90% purity, the main impurity being the product derived from the minor regioisomer 2-t-butoxy-1-propanol (present at about 7% in the starting material). This ester was direct fluorinated as described in U.S. Pat. No. 5,488,142. The resulting solution was analyzed by $^{19}F$ NMR to contain $CF_3OCF(CF_3)CF_2OCOCF_3$ in 43% yield. Methanalysis gave the same methyl ester as Example 13. One could then convert to the perfluorovinyl ether as described above.

Example 15

Perfluoro methyl vinyl ether from methyl 2-methoxypropionate

Methyl 2-methoxypropionate (520.3 g,) was fluorinated in an ECF cell as described in U.S. Pat. No. 2,713,593 equipped with −40° C. and −80° C. condensers. The yield of $CF_3OCF(CF_3)COF$ was estimated as 17%. One could then convert this to perfluoromethylvinyl ether as described above.

Example 16

Perfluoro ethoxymethyl vinyl ether,
$C_2F_5OCF_2OCF=CF_2$

Ethyl 2-ethoxymethoxypropionate was made by stirring and heating a mixture of 1007 g (8.5 mol) ethyl lactate, 2500 ml (20.2 mol) diethoxymethane (DEM), and 5.0 g toluenesulfonic acid hydrate under nitrogen while distilling off a mixture of ethanol and DEM. Fresh DEM was periodically added. After 12 hr, the mixture was cooled, washed with very dilute NaOH, and the product distilled to 1232 g (7.5 mol, 88%) bp 90° C./20 mm. This ester was direct fluorinated as described in U.S. Pat. No. 5,488,142 and the product treated with methanol to give $C_2F_5OCF_2OCF(CF_3)COOMe$ bp 107–112° C. in 30% yield. A crude sample (2342 g, 57% assay, remainder PMM and $CF_3COOMe$) was added to a stirred solution of 300 g NaOH in 800 g water at about 30° C. After stirring 18 hr, the mixture was treated with 1 liter 50% sulfuric acid and the lower phase distilled to 718 g bp 60° C./1 mm as the carboxylic acid. A second batch of 2406 g crude ester yielded 896 g, and rewashing of the combined distillation residues with 50% sulfuric acid yield an additional 412 g, for a total yield of 2029 g of the carboxylic acid. Of this 1000 g was mixed with 500 g powdered sodium carbonate in 2.5 l. acetone for 24 hr, filtered and stripped to give $C_2F_5OCF_2OCF(CF_3)COONa$, a tan solid. A solution of 365.8 g in 200 ml diethyl ether was mixed with 250 ml Fluorinert FC-71 (3M Co.), stripped at 20 mm for 20 min, and heated to 224° C., at which time volatile product began collecting in the dry-ice cooled traps. Heating was continued for 3 hr, final temperature was 245° C. The product, the corresponding perfluorovinyl ether with a bp of 46° C., was recovered by fractionation.

Example 17

Perfluoro ethoxymethyl vinyl ether from 3-chloro-2-(ethoxymethoxy)-1-propyl acetate A mixture of 10.0 g $FeCl_3$ and 276 ml acetic acid was treated slowly with 312 ml epichlorohydrin at 5 to 15° C. (dry-ice bath). The product was mixed with 5.1 g NaOAc and filtered to 497.1 g amber liquid, a 87-13 mixture of $HOCH(CH_2Cl)CH_2OAc$ and $AcOCH(CH_2Cl)CH_2OH$. A solution of 304 g of the above mixture and 200 g $ClCH_2OEt$ in 600 ml methylene chloride was chilled in ice while adding 260 N,N-diisopropyl ethylamine. Distillation yielded 257.0 g bp 80° C./1.2 mm. The major components were identified by gc/ms, $^1H$-NMR, and $^{13}C$-NMR as $C_2H_5OCH_2OCH(CH_2Cl)CH_2OAc$ (65%), $AcOCH(CH_2Cl)CH_2OCH_2OC_2H_5$ (18%) and starting alcohols (13%). Fluorination according to U.S. Pat. No. 5,488,142 and distillation of the PMM solvent left 184.1 g perfluorinated ester as residue. This was treated with about 0.5 ml pyridine, according to U.S. Pat. No. 5,466,877, with vigorous outgassing and formation of $C_2F_5OCF_2OCF(CF_2Cl)COF$, distilled to 90.2 g bp 85–95° C. $^{19}F$-NMR shows this to be 73% pure. One could then convert this to the perfluorovinyl ether as described for other 3-chloro-perfluoro-(2-alkoxypropionates) in U.S. Pat. No. 5,449,825.

Example 18

Perfluoro methyl vinyl ether

Hexafluoropropylene oxide (HFPO, 300 g) was added to 50 g of 25% sodium methoxide in methanol plus 450 g methanol at room temperature in a modification of the procedure of (J. Org. Chem. 31, 2312 (1960) to give $CH_3OCF(CF_3)COOMe$ bp 110–118° C. This was direct fluorinated according to U.S. Pat. No. 5,488,142 and the product was methanolysed to give the same ester as in Example 11. One could then convert this to the perfluorovinyl ether as described above.

Example 19

Perfluoro methyl vinyl ether $CH_3OCF(CF_3)COOMe$ from Example 15 was fluorinated in an ECF cell according to U.S. Pat. No. 2,713,593 to give in 21% yield CF$_3$OCF(CF$_3$)COF. One could then convert this to the perfluorovinyl ether as described above.

Example 20

Perfluoro methyl vinyl ether via 2-methoxy-2,3,3,3-tetrafluoropropionic acid anhydride The adduct of HFPO and methanol from Example 15 was hydrolyzed to the carboxylic acid and dehydrated with P$_2$O$_5$ to give 2-methoxy-2,3,3,3-tetrafluoropropionic acid anhydride, bp 144–146° C. This was direct fluorinated according to U.S. Pat. No. 5,488,142 to give the perfluoro anhydride bp 85–88° C., methanolysis of which yielded CF$_3$OCF(CF$_3$)COOMe bp 76–78° C. which was converted to CF$_3$—O—CF=CF$_2$ bp -23° C.

Example 21

Perfluoro propyl vinyl ether

Hexafluoropropylene (36 g) was added to 20.8 g methyl lactate and about 0.2 g KF in 50 ml DMF at 20–30° C. Distillation yielded a mixture of esters bp 64–76° C./55 mm. This was fluorinated in an ECF cell according to U.S. Pat. No. 2,713,593 to give in about 25% yield a 2:1 mixture of C$_3$F$_7$OCF(CF$_3$)COF and C$_3$F$_7$OC$_2$F$_4$COF. One could then convert these to the corresponding perfluorovinyl ethers as described above.

What is claimed is:

1. A process for the preparation of a perfluorinated vinyl ether of the formula CF$_2$=CF—O—R$_f$ wherein R$_f$ is a linear, branched or cyclic perfluorinated aliphatic group that contains at least one oxygen atom, the process comprising the steps of
    a) providing a hydrocarbon precursor comprising at least one 2-alkoxy propionate moiety, derivative or equivalent that may be partially halogenated;
    b) fluorinating the hydrocarbon precursor to provide a perfluorinated intermediate; and
    c) converting the perfluorinated intermediate to its corresponding perfluorinated acid metal salt, and
    d) converting the perfluorinated acid metal salt to its corresponding perfluorovinyl ether.

2. A process according to claim 1 wherein the hydrocarbon precursor is selected from the group consisting of a hydrocarbon ester, anhydride, acid halide or acid.

3. A process according to claim 2 wherein the hydrocarbon precursor is

R$_h$OCH(CH$_3$)C(O)X$_h$ where R$_h$ is a C$_1$–C$_{20}$ alkyl or aromatic group, which may be linear, branched, cyclic and which may contain additional ether linkages, and X$_h$ is selected from the group consisting of R$^h$, lower alkoxy, OC(O)CH(CH$_3$)OR$_h$, —F and —Cl.

4. A process for the preparation of a perfluorinated vinyl ether of the formula CF$_2$=CF—O—R$_f$ wherein R$_f$ is a linear, branched or cyclic perfluorinated aliphatic group that my contain oxygen atoms, the process comprising the steps of
    a) providing a hydrocarbon precursor comprising at least one 2-alkoxy propionate moiety, derivative or equivalent that may be partially halogenated wherein the hydrocarbon precursor has the formula

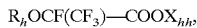

R$_h$OCF(CF$_3$)—COOX$_{hh}$, wherein X$_{hh}$ is —OC(O)CF(CF$_3$)OR$_h$ and wherein R$_h$ is a C$_1$–C$_{20}$ alkyl or aromatic group, which may be linear, branched, cyclic and which may contain additional ether linkages;
    b) fluorinating the hydrocarbon precursor to provide a perfluorinated intermediate; and
    c) converting the perfluorinated intermediate to its corresponding perfluorinated acid metal salt, and
    d) converting the perfluorinated acid metal salt to its corresponding perfluorovinyl ether.

5. A process according to claim 4 wherein the hydrocarbon precursor is provided by reacting hexafluoropropylene oxide and an alcohol of formula R$_h$OH.

6. A process according to claim 4 wherein R$_h$ is linear.

7. A perfluorovinyl ether having the formula R$_f$OCF$_2$OCF=CF$_2$ wherein R$_f$ is a linear, branched or cyclic perfluorinated aliphatic group that may contain oxygen atoms forming additional ether linkages and that does not contain any sites of terminal unsaturation.

8. A perfluorovinyl ether according to claim 9 wherein R$_f$ is —CF$_3$.

9. A perfluorovinyl ether according to claim 9 wherein R$_f$ is —CF$_2$CF$_3$.

10. A process for the preparation of a perfluorinated vinyl ether of the formula CF$_2$=CF—O—R$_f$ wherein R$_f$ is a linear, branched or cyclic perfluorinated aliphatic group that may contain oxygen atoms, the process comprising the steps of
    a) providing a hydrocarbon precursor comprising at least one 2-alkoxy propionate moiety, derivative or equivalent that may be partially halogenated wherein the hydrocarbon precursor is selected from the group consisting of

R'$_h$(OCH(CH$_3$)C(O)X$_h$)$_2$ (i)

wherein R'$_h$ is a divalent, C$_1$–C$_{20}$ alkyl or aromatic group, which may contain additional ether linkages, X$_h$ is selected from the group consisting of R$_h$, lower alkoxy, OC(O)CH(CH$_3$)OR$_h$, —F, and —Cl, wherein R$_h$ is a monovalent C$_1$–C$_{20}$ alkyl or aromatic group, which may be linear, branched, or cyclic and which may contain additional ether linkages, or
    (ii) a reaction product of a fluorinated olefin and an ester of lactic acid;
    b) fluorinating the hydrocarbon precursor to provide a perfluorinated intermediate;
    c) converting the perfluorinated intermediate to its corresponding perfluorinated acid metal salt; and
    d) converting the perfluorinated acid metal salt to its corresponding perfluorovinyl ether.

* * * * *

UNITED STATES PATENT AND TRADEMARK OFFICE
CERTIFICATE OF CORRECTION

PATENT NO. : 6,255,536 B1
DATED : July 3, 2001
INVENTOR(S) : Allan T. Worm, George G.I. Moore, Miguel A. Guerra, Werner Schwertfeger, Klaus Hintzer, Zai-Ming Qiu and Erik D. Hare It is certified that error appears in the above-identified patent and that said Letters Patent is hereby corrected as shown below:

Column 7,
Table 2, Example 5 under Product: "$C_3F_7$-O-CF=$C_2$" should read -- $C_3F_7$-O-CF=$CF_2$ --

Column 12,
Lines 27 and 29, "according to claim 9" should read -- according to claim 7 --
Line 44, "$C_{1-C20}$" should read -- $C_1$-$C_{20}$ --

Signed and Sealed this

Twenty-eighth Day of May, 2002

Attest:

*Attesting Officer*

JAMES E. ROGAN
*Director of the United States Patent and Trademark Office*